US 8,818,746 B1

(12) United States Patent
Johnson et al.

(10) Patent No.: US 8,818,746 B1
(45) Date of Patent: Aug. 26, 2014

(54) CRACK DETECTION IN THICK-WALLED CYLINDERS

(75) Inventors: Mark A. Johnson, West Sand Lake, NY (US); Moayyed A. Hussain, Menands, NY (US); Edward J. Troiano, Schenectady, NY (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 536 days.

(21) Appl. No.: 13/071,691

(22) Filed: Mar. 25, 2011

Related U.S. Application Data

(60) Provisional application No. 61/317,774, filed on Mar. 26, 2010.

(51) Int. Cl.
*G01R 23/16* (2006.01)
*G01N 29/04* (2006.01)
*G01N 29/14* (2006.01)
*G01N 29/46* (2006.01)
*G01N 21/952* (2006.01)

(52) U.S. Cl.
CPC ............. *G01N 29/045* (2013.01); *G01N 29/14* (2013.01); *G01N 29/46* (2013.01); *G01N 21/952* (2013.01); *G01N 2203/006* (2013.01)
USPC .................. 702/77; 702/35; 702/39; 702/76; 702/190

(58) Field of Classification Search
CPC ..... G01N 29/045; G01N 29/14; G01N 29/46; G01N 21/952; G01N 2203/006
USPC .............. 702/35, 39, 54, 71, 76, 77, 141, 190
See application file for complete search history.

(56) References Cited

U.S. PATENT DOCUMENTS

| | | | | |
|---|---|---|---|---|
| 2,517,133 | A | * | 8/1950 | Porter ............................ 73/167 |
| 3,894,425 | A | * | 7/1975 | Winters et al. .................. 73/640 |
| 3,914,996 | A | * | 10/1975 | Davis et al. .................... 73/167 |

(Continued)

OTHER PUBLICATIONS

Zagrai, A., Donskoy, D., and Lottiaux, J. N-Scan: New Vibro-Modulation System for Crack Detection Monitoring and Characterization. American Institue of Physics [online], 2004 [retrieved on Jul. 25, 2013]. Retrieved from the Internet: <http://proceedings.aip.org/resource/2/apcps/700/1/1414_1>.*

*Primary Examiner* — Sujoy Kundu
*Assistant Examiner* — Paul D Lee
(74) *Attorney, Agent, or Firm* — Henry S. Goldfine

(57) ABSTRACT

A simple, inexpensive, and fast method of establishing if a defect does or does not exist within a thick-walled solid geometry, which is especially useful to detect if such a defect, a crack, exists within a gun barrel. With further analysis, the method allows not only the identification of the defect's presence; but, a means of establishing the size thereof—which, for example, is critical to understanding if a gun tube has a defect that would warrant its being taken out of service for the safety of its crew or removed from manufacturing. The method involves creating an acoustic vibration in the particular thick-walled, solid geometry, esp. a gun barrel, and observing the vibration pattern which results. The size of the particular defect can be ascertained by a) manually using a correlation between the magnitude of the defect and the relative changes in the decay coefficient or shifts in frequency data or (b) automatically using a Bayes maximum likelihood, statistical pattern classification algorithm and a library comprised of either the decay coefficients or the means and covariances of defect-free and cracked objects.

6 Claims, 7 Drawing Sheets

(56) References Cited

U.S. PATENT DOCUMENTS 3,916,699 A * 11/1975 Moran et al. ............... 73/623
5,144,838 A *  9/1992 Tsuboi ....................... 73/579
2007/0107777 A1 * 5/2007 Catron ....................... 137/2
2009/0041078 A1 * 2/2009 Yuhas ........................ 374/7
2010/0030492 A1 * 2/2010 Kar et al. .................. 702/39
2011/0054806 A1 * 3/2011 Goldfine et al. ........... 702/34

* cited by examiner

CRACK DETECTION IN THICK-WALLED CYLINDERS

CROSS-REFERENCE TO RELATED APPLICATIONS

This application claims the benefit under 35 USC §119(e) of U.S. Provisional Patent Application No. 61/317,774, filed on Mar. 31, 2010, which is hereby incorporated herein in its totality, by reference.

FEDERAL RESEARCH STATEMENT

The invention described herein may be manufactured, used, and/or licensed by the U.S. Government for U.S. Government purposes.

FIELD OF THE INVENTION

The present invention relates to a method for detecting cracks in thick-walled, cylindrical geometries, such as cannon barrels, using statistical pattern recognition.

BACKGROUND OF THE INVENTION

The safety and performance of gun barrels, i.e. thick-walled cylindrical geometries, can be easily compromised by defects, such as quench cracks are an issue during manufacture, trauma cracks that occur due to rough handling, and stress cracks that develop under the forces related to firing, as well as, under the environmental conditions of, and handling in, the field. Currently, typical military practice is visual and magnetic particle inspection to identify cracks during manufacture and only visual inspection once the gun is fielded. However, visual inspections will not disclose insipient cracks internal to the barrel material and proposed automated systems that scan the inside diameter of gun barrels—in both manufacture and in the field—are complex, bulky, expensive, and relatively slow.

Various dynamic methods are known for identifying and quantifying structural damage, such as stress cracks, as a change in fundamental resonant frequencies occur due to such a defect in a solid structure. The change in frequencies can often be used to detect and locate the defect, even in the presence of ambient noise. A significant amount of work in the field relates to one dimensional problems, dealing with cracked beams under axial and transverse vibration—due to the ease of modeling a real beam or rod and thereby simplifying the analysis. Particular examples of such work including a simple theory of cracked beam under axial and transverse vibrations, presented by Y. Narkis, Journal of Sound and Vibration 172(4), 549-558 (1994). Other work by P. F. Rizos et al., Journal of Sound and Vibration 138, 381-388, 475-488 (1990) and A. D. Dimarogonas, Engineering Fracture Mechanics 55(5), 831-857 (1996), also disclose such methods and review the field of crack detection using frequency spectra. Mathematical models are developed that simulate a crack as a linear spring for axial motion and as a torsion spring under transverse motion. The compliance of these springs is represented by the stress intensity factor based upon disclosures by G R Irwin, et al., Fundamental Aspect of Crack Growth and Fracture, Fracture. An Advanced Treatise, Vol. III. Engineering Fundamentals and Environmental Effects, edited by H. Liebowitz, Academic Press, New York, 1971, pp. 2-46. In all of these papers, it is shown that the natural frequencies of cracked rods and beams shift to lower values under axial or transverse loads because of the increased compliance.

A particular dynamic method was disclosed by A. Morassi, in a paper titled: Identification of a Crack in a Rod Based On Changes in a Pair of Natural Frequencies, Journal of Sound and Vibration, 242(4), 577-596 (2001), wherein a series of calculations and experiments were presented with a hypothesis expecting more reliable results, when the damage being identified was less severe and lower order frequencies were considered. Morassi concluded that his analytical model, with these factors of less damage and lower frequencies, proved extremely accurate—the percentage discrepancy between the measured and analytical values of the involved natural frequencies being lower than 1% within the 30th vibrating mode. Morassi's method included a series of experiments using an impulse force hammer to excite a steel rod of square solid cross-section to detect notches of increasing depth (damage)—the rod suspended by two steel wire ropes to simulate free-free boundary conditions, with the axial response measured by a piezoelectric accelerometer fixed in the center of an end cross-section of the rod. The vibration signals were acquired by a dynamic analyzer and then determined in the frequency domain to measure the relevant frequency response term (inertance)—using methodology detailed in a 1997 article by A. Morassi, in Inverse Problems in Engineering, 4, 231-254, titled "A Uniqueness Result on Crack Location in Vibrating Rods".

An alternative dynamic method using impact-acoustic resonance, including Impulse Resonance Acoustic Spectroscopy (IRAS), was detailed by A. Sutin, in a presentation at the 35th Annual Review of Progress in Quantitative Nondestructive Evaluation, Chicago, Ill., 2008—the presentation titled: "Application of Impulse Resonant Acoustic Spectroscopy (IRAS) for Crack Detection in Pipes". In IRAS, a laser vibrometer is used to detect the vibration of the specimen's surface using a laser vibrometer. The spectra of the received laser signal is analyzed using FFT, to transform the signal to the frequency spectrum, such that the narrow frequency band about the specimens' resonance frequency can be filtered and isolated, and the envelope function of that filtered signal established—which will indicate a clear splitting of the resonance frequency envelope in the presence of a crack. This methodology has been demonstrated on thin walled solid geometries, such as casing pipes, and obviously involves significant expense.

Thus there is a need in the art for a relatively low cost, simple and relatively fast method of determining the presence and location of cracks in thick walled cylindrical geometries—as it has been surprisingly found that (1) the simple one dimensional model of a cracked geometry does not apply to cylindrical geometries, (2) that some fundamental frequencies may not be affected by a crack because of its orientation.

SUMMARY OF INVENTION

The present invention addresses the need for a relatively inexpensive, simple and fast method to detect defects, esp. cracked, thick-walled, cylindrical geometries, such as gun barrels—which must be tested for such cracks during manufacture and in the field. The invention employs statistical pattern recognition using changes in the fundamental modes of vibration that arise following an impulse load to identify a flawed sample. Surprisingly, the expected frequency shifts and splits resulting from a defect, or crack, were not always observed at the lower frequencies, as would have been expected based upon the teachings of the prior art. Also, the effect of the crack on frequency splitting and damping was found to be more dramatic for the most damage, i.e. the deepest crack.

The present invention provides a method for establishing if a thick-walled, cylindrical geometry is defect free or if there is a defect therein, the method involving the steps of: (1) creating an acoustic vibration in that geometry; (2) detecting the vibration which results; (3) filtering that signal, to remove extrinsic noise; and (4) analyzing the resulting frequency pattern of the vibration by (a) using a Fourier transform to decompose the filtered frequency signal into its constituent major frequencies or spectrum; (b) computing the decay coefficient of the time series data; whereby, it can be ascertained if a defect exists. If, relative to a defect-free sample, there is no change in the decay envelope of the vibration pattern over time and no shift or splitting of the fundamental modes of vibration, it means that there are no defects in the subject thick-walled, cylindrical geometry. However, if, relative to a defect-free sample, the vibration pattern of the decay envelope is that of a series of hi-low amplitudes/waves; or the envelope of the vibration pattern decays more quickly; or if there is a shift or splitting of the fundamental modes of vibration, i.e. there is a shift or splitting of the modes of vibration relative to a defect free baseline, then a defect has been identified within the subject thick-walled cylindrical geometry. The hi-low amplitudes are a superposition of the fundamental modes of vibration associated with the two geometries of the defective sample—one with the crack open and one with the crack closed. Interestingly, where a defect was found, changes were not always observed at lower frequencies—which may likely be due to the orientation of the defects being axial. Defects in an axial orientation will not significantly alter the low frequency transverse modes, but will affect the higher frequency breathing modes.

The present invention provides a means for further refining the detection of a defect in a thick-walled, cylindrical geometry, so as to establish the degree of that defect, i.e. the length of the crack or defect. Establishing the degree of the defect can be critical, as, for example, the barrel of a field piece, such as a howitzer, can be functional with one or a series of very minor cracks therein; however, it any particular crack exceeds a particular dimension, depending upon the caliber of the shell being fired/the size of the barrel, there is a danger of the barrel exploding and it must be taken out-of-service. To establish the length of a crack the analysis of the filtered vibration pattern, detailed above, requires an additional step. The relative change in the decay coefficient associated with the time series data or the degree to which the fundamental frequencies shift in the frequency domain can be used to determine the magnitude of the defect. The correlation between the size of the defect and the change in the decay coefficient or shift in frequencies can be done manually or using an automatic classifier. Therefore, looking at the method from the beginning—one must (1) create an acoustic vibration in the thick-walled, cylindrical geometry; (2) detect the vibration which results; (3) filter that signal, to remove extrinsic noise; (4) analyze the resulting frequency pattern of the vibration by (a) using a Fourier transform to decompose the filtered frequency signal into its constituent major frequencies or spectrum, (b) computing the decay coefficient of the time series data; (5) determine the severity of the defect either (a) manually using a correlation between the magnitude of the defect and the relative changes in the decay coefficient or shifts in frequency data, or (b) preferably, automatically using a Bayes maximum likelihood, statistical pattern classification algorithm and a library comprised of either the decay coefficients or the means and covariances of defect-free and cracked objects, for comparison.

Preferably, the methodology of the present invention to a defect, or crack, in a thick-walled, cylindrical geometry, such as a gun tube, e.g. a 105 mm, 120 mm, 155 mm, 175 mm, or 203 mm gun-artillery tube or the like, uses any significant vibration that naturally occurs within/to the particular geometry—so, in the case of a gun tube, it would be the vibrations resulting from the firing of the gun, regarding which the gun tube is a part. Alternatively, a vibration created with a hammer, such a calibrated hammer is preferred, such as a 3 lb modally tuned impact hammer (to obtain a significant initial vibration), or other appropriate hard object, such as a crow bar or sledge hammer—the location of which impact does not matter.

Preferably, the detecting of the acoustic vibration of the strike is detected using two or more accelerometers, with accelerometers located at a single or multiple axial distances and circumferentially, around the outside diameter of the cylinder. It is critical that at least one of the two or more accelerometers not be directly atop the defect—in order to obtain a vibration pattern to detect the defect. Therefore, it is best to space the at least two accelerometers at least 90 degrees apart, and at different axial locations, to obtain a significant spatial separation. Further, the accelerometers must have sufficient frequency response to capture all of the fundamental modes of interest—such as PCB Piezotronics, Inc. Model 309A accelerometers.

As detailed above, the vibration data from the accelerometers is filtered so that only the frequencies corresponding to the natural modes of vibration are analyzed. The vibration pattern output from the filter can be manually observed and compared to defect free samples from similar thick-walled, solid geometries, to establish if the particular geometry is defect free or contains a defect. Or, the vibration pattern output from the filter can be fed into a general purpose computer to automatically establish if there is a defect and the size thereof, using a Bayes maximum likelihood, statistical pattern classification algorithm and a library comprised of either the decay coefficients or the means and covariances of defect-free and cracked objects, for comparison.

The nature of the subject invention will be more clearly understood by reference to the following detailed description and the appended claims.

DETAILED DESCRIPTION OF THE INVENTION

Figure 1:
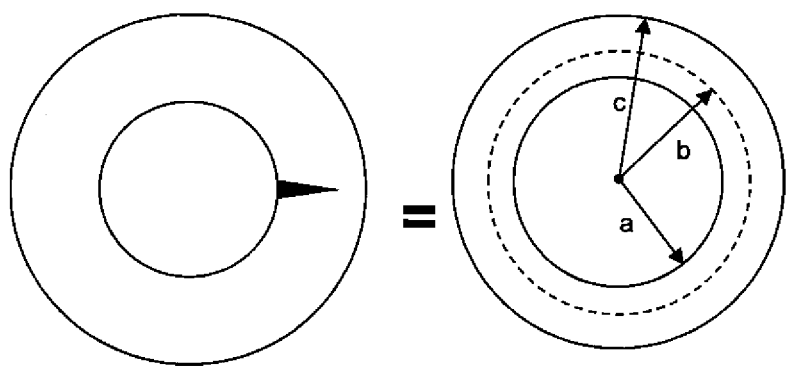
FIG. 1. is a cracked thick-walled cylinder and the equivalent representation of the mathematical model for guided waves.

The methodology of the present invention involves modeling the effects of a defect or crack on the natural modes of vibration of a thick walled cylinder, such as may typically include artillery gun barrels, such as 105 mm, 120 mm, 155 mm, 175 mm and/or 203 mm gun-artillery barrels and the like. A model of a cracked, thick-walled cylinder was developed, because the simple one dimensional model of a cracked geometry represented by two sections connected by an axial or torsional spring used by the prior art does not apply to the present cylindrical geometries of interest. The present model of a cracked cylinder involves considering two concentric cylinders connected by a torsional spring with a compliance approximately equal to the stress intensity factor. This model is designed to illustrate the frequency shift and frequency splitting using the dispersion characteristics of tangentially guided and standing waves. The dispersion curves are generated from the travelling waves along the circumferential direction and the extracted standing waves. The model is shown in FIG. 1 where the torsional springs have been omitted.

Proper boundary conditions are essential to accurately model the cracked geometry. For the model in FIG. 1, assuming the concentric rings have identical material properties, the free stress conditions on the inner and outer radii are given by:

$$\sigma_r(a,\theta)=0 \quad (1)$$

$$\tau_{r\theta}(a,\theta)=0 \quad (2)$$

$$\sigma_r(c,\theta)=0 \quad (3)$$

$$\tau_{r\theta}(c,\theta)=0 \quad (4)$$

The boundary conditions for continuity at the interface are given by:

$$u_{r1}(b,\theta)=u_{r2}(b,\theta) \quad (5)$$

$$\tau_{r1}(b,\theta)=\tau_{r2}(b,\theta) \quad (6)$$

$$\sigma_{r1}(b,\theta)=\sigma_{r2}(b,\theta) \quad (7)$$

where subscript 1 refers to the inner ring and subscript 2 refers to the outer ring. The crack jump condition at the interface is given by:

$$\{\varepsilon_{\theta 1}(b,\theta) - \varepsilon_{\theta 2}(b,\theta)\} = \frac{\Theta}{Ex^{*2}}\{\sigma_{\theta 1}(b,\theta) - \sigma_{\theta 2}(b,\theta)\} \quad (8)$$

Where, x* is non-dimensional crack length. Equations 1-8 model a cracked interface at which the normal and tangential stresses are continuous, but the jump in circumferential strains is proportional to jump in circumferential stresses. The coefficient $\Theta$ represents the normalized compliance (inverse of spring constant). The value of $\Theta$ goes to zero for a defect free cylinder. The equation of equilibrium in terms of displacement $\bar{u}$ is completely disclosed and documented by J. L. Rose, Ultrasonic Waves in Solid Media, Cambridge University Press, New York, 1999 and given by $$(\lambda+2\mu)\nabla(\nabla \cdot \vec{u}) - \mu\nabla \times \nabla \times \vec{u} - \rho\frac{\partial^2 \vec{u}}{\partial^2 t} = 0 \quad (9)$$

The displacement in terms of scalar and vector potentials is:

$$\vec{u} = \nabla\phi + \nabla \times \vec{\psi} \quad (10)$$

and the governing differential equation for scalar and vector potentials are the wave equations:

$$\nabla^2\phi - \frac{1}{V_l^2}\frac{\partial^2 \phi}{\partial t^2} = 0 \quad (11)$$

$$\nabla^2\vec{\psi} - \frac{1}{V_s^2}\frac{\partial^2 \vec{\psi}}{\partial t^2} = 0 \quad (12)$$

where the dilatational and shear velocities, in terms of elastic constants, are:

$$V_l^2 = \frac{\lambda+2\mu}{\rho} \quad (13)$$

$$V_s^2 = \frac{\mu}{\rho} \quad (14)$$

Since breathing modes are of interest, we consider waves traveling along the circumferential direction. These will be traveling waves with n=kb, with k to be determined from a frequency equation. The solution for such circumferential waves, for the inner ring and the outer ring can be represented as:

$$[S_1]=A\phi_{j1}+B\phi_{y1}+C\psi_{j1}+D_{y1} \quad (15)$$

$$[S_2]=E\phi_{j2}+F\phi_{y2}+G\psi_{j2}+H\psi_{y2} \quad (16)$$

where A to H are the superposition constants and the symbols, in terms of Bessel functions, are defined as:

$$\phi_{j1} = J_n(\alpha r)e^{i(n\theta-\omega t)} \quad (17)$$

$$\phi_{y1} = Y_n(\alpha r))e^{i(n\theta-\omega t)} \quad (18)$$

$$\psi_{j1} = J_n(\beta r)e^{i(n\theta-\omega t)} \quad (19)$$

$$\psi_{y1} = Y_n(\beta r)e^{i(n\theta-\omega t)} \quad (20)$$

$$\phi_{j2} = J_n(\alpha r)e^{i(n\theta-\omega t)} \quad (21)$$

$$\psi_{y2} = Y_n(\alpha r))e^{i(n\theta-\omega t)} \quad (22)$$

$$\psi_{j2} = J_n(\beta r)e^{i(n\theta-\omega t)} \quad (23)$$

$$\psi_{y2} = Y_n(\beta r)e^{i(n\theta-\omega t)} \quad (24)$$

where, $$\alpha^2 = \frac{\omega^2}{V_l^2} \quad (25)$$

$$\beta^2 = \frac{\omega^2}{V_s^2} \quad (26)$$

$$n = kb \quad (27)$$

$$k = \frac{\omega}{c} \quad (28)$$

Only the z component of vector potential is required. The potentials can be computed by neglecting the $e^{-i\omega t}$ term, using the definition of displacement, and computing strains and stresses. The J (Besse) function of first kind) solution is given as:

$$\phi_{j1} = J_n(\alpha r)e^{in\theta} \tag{29}$$

$$u_r(r, z) = \frac{\alpha}{2}[(J_{n-1}(\alpha r) - J_{n+1}(\alpha r))]e^{in\theta} \tag{30}$$

$$u_\theta(r, z) = \frac{i\alpha}{2}[(J_{n-1}(\alpha r) + J_{n+1}(\alpha r))]e^{in\theta} \tag{31}$$

$$\varepsilon_\theta = -\frac{\alpha^2}{4}[(J_{n-2}(\alpha r) + 2J_n(\alpha r) + J_{n+2}(\alpha r))]e^{in\theta} \tag{32}$$

$$\varepsilon_{r\theta} = \frac{i\alpha^2}{8}[(2J_{n-2}(\alpha r) - 2J_{n+2}(\alpha r))]e^{in\theta} \tag{33}$$

$$\sigma_r = \frac{\mu\alpha^2}{2}[(J_{n-2}(\alpha r) - 2(\chi^2 - 1)J_n(\alpha r) + J_{n+2}(\alpha r))]e^{in\theta} \tag{34}$$

$$\sigma_\theta = -\frac{\mu\alpha^2}{2}[(J_{n-2}(\alpha r) + 2(\chi^2 - 1)J_n(\alpha r) + J_{n+2}(\alpha r))]e^{in\theta} \tag{35}$$

$$\tau_{r\theta} = 2\mu\varepsilon_{r\theta} \tag{36}$$

$$\psi_{j1} = J_n(\beta r)e^{in\theta} \tag{37}$$

$$u_r(r, z) = \frac{i\beta}{2}[(J_{n-1}(\beta r) - J_{n+1}(\beta r))]e^{in\theta} \tag{38}$$

$$u_\theta(r, z) = -\frac{\beta}{2}[(J_{n-1}(\beta r) - J_{n+1}(\beta r))]e^{in\theta} \tag{39}$$

$$\varepsilon_\theta = \frac{i\beta^2}{4}[(J_{n-2}(\beta r) - J_{n+2}(\beta r))]e^{in\theta} \tag{40}$$

$$\varepsilon_{r\theta} = -\frac{\beta^2}{8}[(2J_{n-2}(\alpha r) + 2J_{n+2}(\alpha r))]e^{in\theta} \tag{41}$$

$$\sigma_r = \frac{i\mu\beta^2}{2}[(J_{n-2}(\beta r) - J_{n+2}(\beta r))]e^{in\theta} \tag{42}$$

$$\sigma_\theta = \frac{i\mu\beta^2}{2}[(-J_{n-2}(\beta r) + J_{n+2}(\beta r))]e^{in\theta} \tag{43}$$

$$\tau_{r\theta} = 2\mu\varepsilon_{r\theta} \tag{44}$$

The Y solution is obtained by substituting Y for J. If the torsional case is neglected and boundary equations 1-7 are applied to equations 29-44, the result is 8 homogenous equations. The existence of a nontrivial solution gives the determinant, the zeroes of which provide the dispersion relation of velocities verses frequencies. Sixty four elements of the determinant $\{D_{ij}\}$ can be selected from the complete solution given in equations 29-44 with the corresponding solution for Bessel function J replaced by Y.

Figure 2:
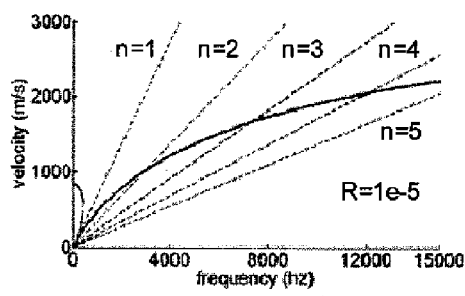
FIG. 2. is dispersion curves for a model of a defect free ($R=1e^{-5}$) and cracked ($R=0.882$) sample. The dashed straight lines correspond to standing waves.
Figure 2:
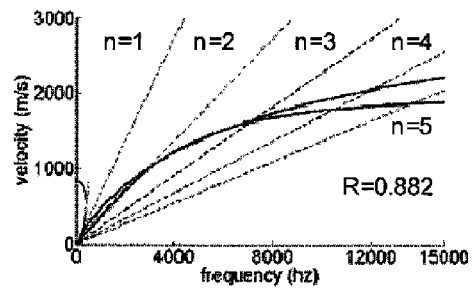

The dispersion relations were determined for four values of $$R = \Theta\frac{\mu}{Ex^{*2}}$$

for a thick-walled cylinder with a uniform inner and outer diameter. Using the definition of n and k given in equation 27, the standing modes can be computed as the intersection of n with the dispersion curves. If there is no crack, only one dispersion curve appears for low velocities FIG. 2 shows the dispersion curves and standing waves for n=1 to 5 for a defect free (R=1e$^{-5}$) and large crack (R=0.882). The figure shows two main branches of the dispersion curve that appear for the large value of R. The intersection of n=2 with the main branch of dispersion curve gives first natural frequency of vibration. Higher modes are obtained with larger values of n. As R increases, the two main dispersion curves overlap. The standing wave frequencies for R=1e-5 are 3000 Hz (n=2), 7345 Hz (n=3), and 12050 Hz (n=4). The two intersection points with n=2 gives the split in the frequency into components $f_1$ and $f_2$, and the decrease in natural frequency. The model clearly predicts the phenomena of frequency reduction and frequency splitting. The frequencies for R=0.882 are $f_1$=3023 Hz and $f_2$=2852 Hz for n=2. The splitting of frequencies in the higher order modes (n>2) for this model is not meaningful.

G. R. Irwin. and P. C. Paris. show how compliances can be related to stress intensity factors and how these values can be determined experimentally as completely disclosed and documented in Fundamental Aspects of Crack Growth and Fracture. Fracture. An Advanced Treatise, Vol. III. Engineering Fundamentals and Environmental Effects, edited by H. Liebowitz, Academic Press, New York, 1971, pp. 2-46. Considering a plane stress case of a thin plate of width W and thickness B with an edge crack of length x, it can shown that compliance C=L/P can be related to energy release rate per unit thickness B by:

$$\wp = \frac{1}{2}\frac{P^2}{B}\left(\frac{dC}{dx}\right) \tag{45}$$

where P is load and L is displacement. Equating (45) to the energy release rate for a plane stress condition and unit thickness we have:

$$\wp = \frac{1}{2}\frac{P^2}{B}\left(\frac{dC}{dx}\right) = \frac{k^2}{E} \tag{46}$$

The normal form of stress intensity factor can be represented as: k=FAC$\sigma\sqrt{\pi x}$, where FAC is computed analytically or numerically for various crack configurations. Substituting this definition of k into (46) and integrating in terms of non-dimensional crack depth with respect to width W, $$x^* = \frac{x}{W},$$

we have the compliance for B=1 as $$C = \frac{\pi}{B}\frac{x^{*2}}{E}(FAC)^2.$$

Our definition of $$R = \frac{\theta\mu}{Ex^{*2}}$$

gives:

$$R = \pi\frac{\mu}{E}(FAC)^2 \tag{47}$$

The results shown in FIG. 2 for R=0.882 gives FAC=0.85. This is reasonable for a surface crack in a thick-walled cylinder. This simplified analysis can be expanded for specific cases. This model clearly predicts softening and frequency split.

Experimental Results

Figure 3:
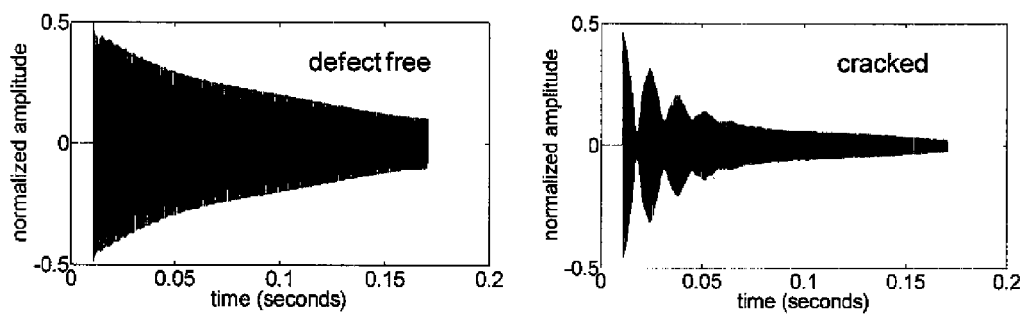
FIG. 3. shows the filtered response of defect free and cracked sample to an impulse load—of the present invention.

Three samples of a large, thick-walled cylinder were tested to prove the efficacy of the present inventive methodology. The first sample had no defects, and each of the other two contained a single crack extending the entire length of the sample. The depth of the crack was different in each of the two defective samples. Two accelerometers were mounted at a single axial, but various circumferential positions around the outside diameter of each of the three samples. Raw vibration data was collected using a calibrated hammer to generate an impulse load. Approximately 200 spectral signatures were collected for each of the three samples and filtered using a low pass filter with a cutoff frequency near the fundamental mode of vibration of interest. FIG. 3 shows the typical response of the defect free and a cracked sample to an impulse load. The data was filtered using a cutoff frequency of 3100 Hz, which is near the first fundamental mode. The figure shows the larger decay coefficients and the beat frequency associated with a cracked sample—clearly and distinctly different from that of the defect free sample. The effect of the crack on frequency splitting and damping is more dramatic for the sample with the deepest crack. The resonant frequency of the defect free sample, sample 1, is 3104 Hz. The split frequencies for the sample with the shallow crack are $f_1$=3099 Hz and $f_2$=3023 Hz. This corresponds to a beat frequency, $f_1-f_2$, of 76 Hz. The split frequencies for the sample with the deep crack are $f_1$=3105 Hz and $f_2$=3088 Hz with a beat frequency of 17 Hz. The damping coefficient, alpha, was extracted from a least squares fit to the exponential form $Ae^{-\alpha}$ using peaks of the averaged data. Alpha was determined to be 8.8 for the defect free sample, 20.2 for the sample with a shallow crack, and 31.2 for the sample with the deepest crack.

Figure 4:
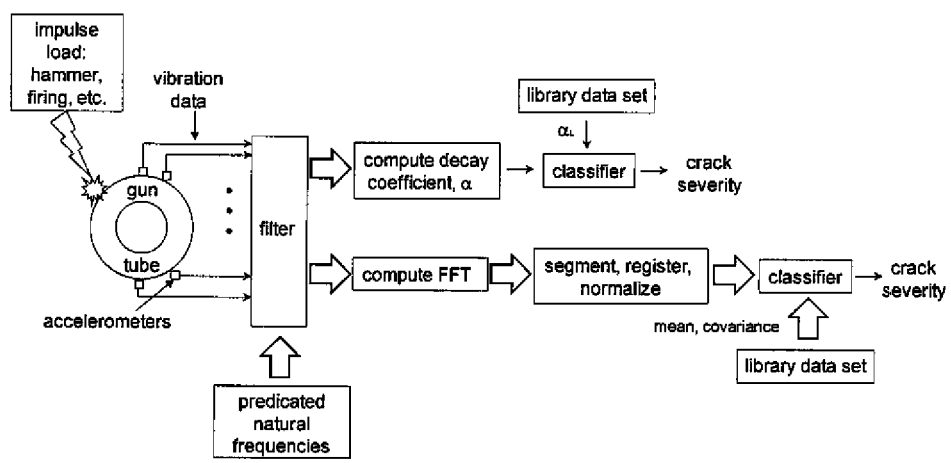
FIG. 4 is a schematic of the automatic crack detection system using either the decay coefficient of the time series data or the frequency spectrum to detect a defect.
Figure 5:
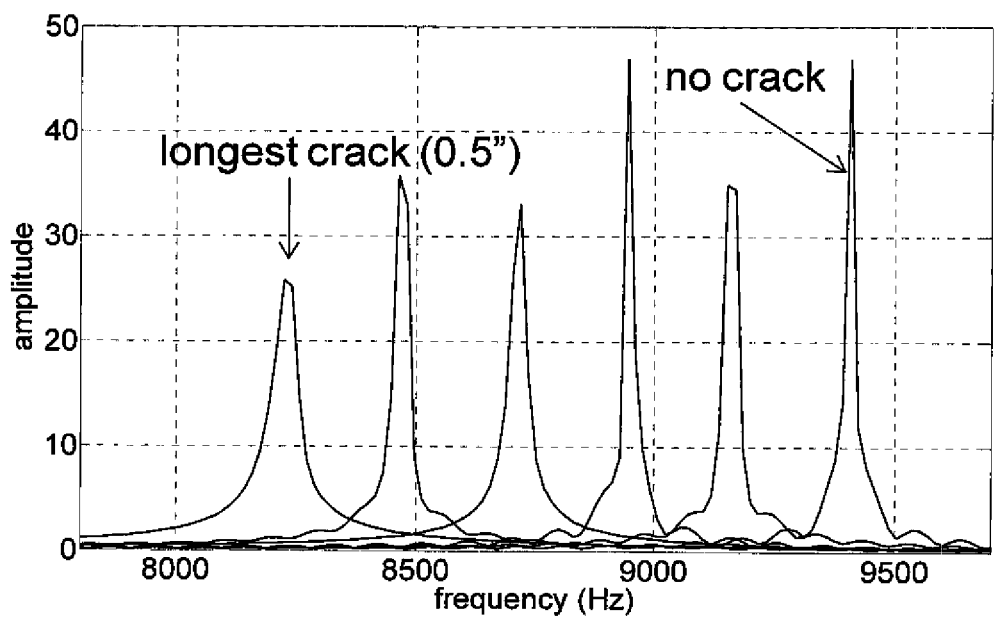
FIG. 5 is a graph showing the second fundamental frequency for different crack lengths.
Figure 6:
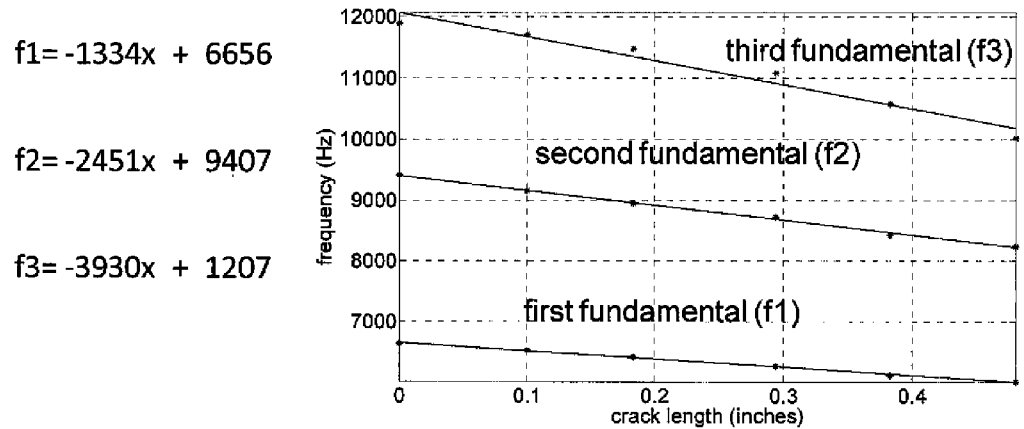
FIG. 6 is a graph showing the first 3 fundamental modes vs. crack lengths.

Clearly, the results demonstrate that the subject inventive method is sensitive to the magnitude of cracks in thick-walled, cylindrical geometries, such as gun tubes. However, further experiments were done using a compact tensile specimen was used in a systematic study that quantified the propagation of a crack in terms of changes in the fundamental modes of vibration. A crack was induced in the tensile specimen and grown in regular increments. Raw vibration data was collected at each increment (in this case 0.1 inches) using the setup in FIG. 4, using frequency data and with the gun tube replaced by the tensile specimen. The raw vibration data was conditioned to extract the only the first 3 fundamental modes using a low pass filter with a cutoff frequency at the third fundamental. FIG. 5 shows the change in frequency data for the second fundamental (9407 Hz, defect free). Results are similar for the modes 1 and 3. FIG. 6 shows the linear fit for the change in frequencies vs. crack length. FIG. 6 also shows the coefficients for the 3 resonant modes analyzed. The large sensitivity coefficients ($|df/dx|>1000$) clearly demonstrate the capability of acoustic impact inspection to monitor and predict the propagation of a crack.

Automatic Statistical Pattern Classification

In the analysis the results of the above experiments under the present inventive methodology, a simple Bayes maximum likelihood, statistical pattern classification algorithm is employed to automatically classify the samples (such methodology are completely disclosed and documented by K. Fukunaga, Statistical Pattern Recognition, Academic Press, San Diego, 1990 and R. Duda, et al, Pattern Classification, Wiley Inter-Science, New York, 2001, which materials are incorporated herein by reference). The magnitude of the spectrum data collected from the accelerometers was filtered, segmented, registered, and normalized for use as the classifier feature. The data was filtered using a lowpass filter with a cutoff frequency of 10250 Hz, which is near the $3^{rd}$ natural frequency of the sample. The feature was comprised of 800 frequencies from the original 16K frequencies in each data set. This feature inherently incorporates the frequency shift, beat frequency, and decay coefficient of the signal. The data was assumed to follow a near normal distribution since the log of the magnitude was used in the analysis. It was also assumed that all spectrums have identical distributions and that each class has equal probability of occurrence. These assumptions are reasonable given that although the dimensionality is large, the intrinsic dimensionality, corresponding to a few parameters, is fairly small. Of the 200 data sets collected for each sample, 100 were used for training and 100 for testing. The training data was used to generate the classifier library. The library was comprised of the mean and covariance of the frequency set for each sample. There were very few peaks in the spectrum so the covariance matrix was ill-conditioned. Therefore, the pseudo inverse and an arbitrarily small threshold was used in the analysis. Using the notation given by Fukunaga and Duda: L, the number of classes, was 3. N, the number of samples in each class, was 100. n, the dimensionality of the samples, was 800 (spectrum peaks from DC to 13 kHz).

Figure 7:
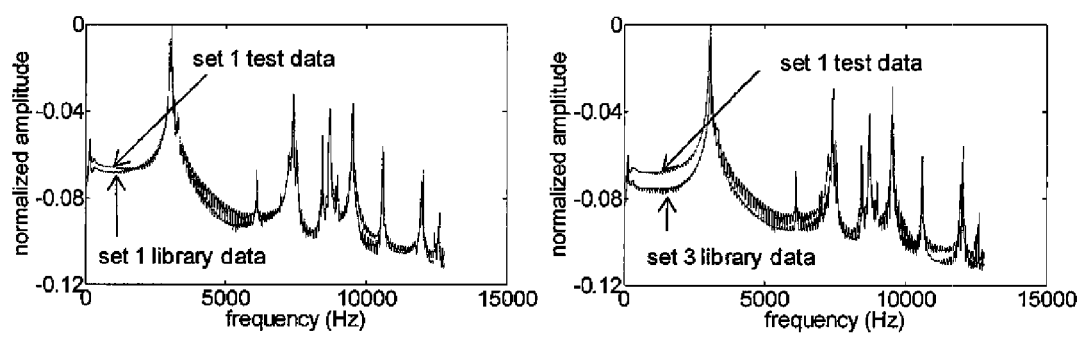
FIG. 7. is a typical result from a set test, test 1—without any defects, against a library result of the tests from that set test 1 data and a second set of data, set test 3—with a defect.

The 100 data sets from each sample were tested using a running average over 7 samples to simulate the average response of the 7 accelerometers envisioned for use in a prototype inspection system. FIG. 7 shows typical results. It gives a comparison of normalized test data collected from sample 1 with the library data (mean) for samples 1 and 3. The Bayes classifier correctly associated test data with a cracked (samples 2 or 3) or the defect free (sample 1) in all cases. The classifier correctly associated the data from the defective samples with the correct sample (sample 2 or 3) in 87% of the cases—a statistically very significant result.

We claim:

1. A method for establishing the size of a defect in a thick-walled, cylindrical geometry comprising, (1) creating an acoustic vibration in that geometry; (2) detecting the vibration which results; (3) filtering that signal, to remove extrinsic noise; and (4) analyzing, on a general purpose computer, the resulting frequency pattern of the vibration by (a) using a Fourier transform to decompose the filtered frequency signal into its constituent major frequencies or spectrum; (b) computing the decay coefficient of the time series data; and (5) using a Bayes maximum likelihood statistical pattern classification algorithm to compare this decay coefficient to a library containing the decay coefficients of similar thick-walled, cylindrical geometries with varying size cracks therein, to determine the particular crack size thereof by correlating with the library data.

2. The method for establishing the size of a defect in a thick-walled, cylindrical geometry of claim 1, wherein said thick-walled, cylindrical geometry is a gun barrel.

3. The method for establishing the size of a defect in a thick-walled, cylindrical geometry of claim 2, wherein said gun barrel is the gun barrel selected from the group consisting of a 105 mm, a 120 mm, a 155 mm, a 175 mm, and a 203 mm artillery gun barrel.

4. The method for establishing the size of a defect in a thick-walled, cylindrical geometry of claim 2, wherein the acoustic vibration within the gun barrel is created by the firing of the gun.

5. The method for establishing the size of a defect in a thick-walled, cylindrical geometry of claim 2, wherein the acoustic vibration within the gun barrel is created by striking the barrel with a hammer.

6. The method for establishing the size of a defect in a thick-walled, cylindrical geometry of claim 1, wherein said detecting the vibration is by means of two or more accelerometers located circumferentially around the outside diameter of the cylindrical geometry.

* * * * *